US00PP31057P3

(12) United States Plant Patent
Moen

(10) Patent No.: US PP31,057 P3
(45) Date of Patent: Nov. 12, 2019

(54) ***GERBERA* PLANT NAMED 'GARSWEETCARO'**

(50) Latin Name: *Gerbera hybrida*
Varietal Denomination: Garsweetcaro

(71) Applicant: Melchior Moen, Mijdrecht (NL)

(72) Inventor: Melchior Moen, Mijdrecht (NL)

(73) Assignee: Florist Holland B.V., Aalsmeer (NL)

( * ) Notice: Subject to any disclaimer, the term of this patent is extended or adjusted under 35 U.S.C. 154(b) by 0 days.

(21) Appl. No.: 15/932,282

(22) Filed: Feb. 16, 2018

(65) Prior Publication Data

US 2018/0255689 P1 Sep. 6, 2018

Related U.S. Application Data

(60) Provisional application No. 62/600,830, filed on Mar. 3, 2017.

(51) Int. Cl.
*A01H 5/02* (2018.01)
*A01H 6/14* (2018.01)

(52) U.S. Cl.
USPC ..... Plt./357
CPC ..... *A01H 6/1456* (2018.05)

(58) Field of Classification Search
USPC ..... Plt./357
CPC . A01H 5/02; A01H 5/00; A01H 5/025; A01H 6/1456
See application file for complete search history.

(56) References Cited

PUBLICATIONS

Flori Line For every season 2018-2019 Seeds and Seedling, retrieved on Feb. 4, 2019, retrieved from the Internet at https://www.kaneya-ltd.co.jp/wp-content/themes/Thema_kaneya/img/seed/florist/pdf/florist.pdf, cover page, 10, 12. (Year: 2019).*
Gro 'n Sell 2016-2017 Catalog, retrieved on Feb. 4, 2019, retrieved from the Internet at http://www.messickco.com/uploads/GroNSellCatalog-2016-2017.pdf, cover page and p. 18 (Year: 2017).*
Meadowlands Hortucultural Inc. 2016-2017 *Gerbera* Program, retrieved on Feb. 4, 2019, retrieved from the Internet at http://www.meadowlandsinc.com/wp-content/uploads/2015/07/2017-MHI-Gerbera-Program-CAN.pdf, pp. 1-7. (Year: 2017).*

* cited by examiner

*Primary Examiner* — June Hwu
(74) *Attorney, Agent, or Firm* — C. A. Whealy

(57) ABSTRACT

A new and distinct cultivar of *Gerbera* plant named 'Garsweetcaro', characterized by its compact, broadly upright and uniformly mounding plant habit; dense and bushy appearance; numerous inflorescences with bright orange-colored ray florets with yellow-colored apices; upright and strong scapes; and good garden performance.

1 Drawing Sheet

Botanical designation: *Gerbera hybrida.*
Cultivar denomination: 'GARSWEETCARO'.

BACKGROUND OF THE INVENTION

The present invention relates to a new and distinct cultivar of *Gerbera* plant, botanically known as *Gerbera hybrida* and hereinafter referred to by the cultivar name 'Garsweetcaro'.

The new *Gerbera* plant is a product of a planned breeding program conducted by the Inventor in De Kwakel, The Netherlands. The objective of the breeding program is to create new compact garden *Gerbera* plants with numerous attractive inflorescences, resistant to cold temperatures and good garden performance.

The new *Gerbera* plant originated from a cross-pollination made during the spring of 2011 in De Kwakel, The Netherlands of a proprietary selection of *Gerbera hybrida* identified as code number 08T013, not patented, as the female, or seed, parent with a proprietary selection of *Gerbera hybrida* identified as code number 09T231, not patented, as the male, or pollen, parent. The new *Gerbera* plant was discovered and selected by the Inventor as a single flowering plant within the progeny of the stated cross-pollination in a controlled greenhouse environment in De Kwakel, The Netherlands during the summer of 2012.

Asexual reproduction of the new *Gerbera* plant by vegetative stem cuttings in a controlled environment in De Kwakel, The Netherlands since the autumn of 2013 has shown that the unique features of this new *Gerbera* plant are stable and reproduced true to type in successive generations.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Garsweetcaro'. These characteristics in combination distinguish 'Garsweetcaro' as a new and distinct *Gerbera* plant:

1. Compact, broadly upright and uniformly mounding plant habit.

2. Dense and bushy appearance.
3. Numerous inflorescences with bright orange-colored ray florets with yellow-colored apices.
4. Upright and strong scapes.
5. Good garden performance and relatively tolerant to cold temperatures.

Plants of the new *Gerbera* differ primarily from plants of the female parent selection in the following characteristics:

1. Plants of the new *Gerbera* have broader leaves than plants of the female parent selection.
2. Plants of the new *Gerbera* have larger inflorescences than plants of the female parent selection.
3. Plants of the new *Gerbera* have shorter scapes than plants of the female parent selection.

Plants of the new *Gerbera* differ primarily from plants of the male parent selection in inflorescence size as plants of the new *Gerbera* have larger inflorescences than plants of the male parent selection.

Plants of the new *Gerbera* can be compared to plants of the *Gerbera hybrida* 'Garglow Imp', disclosed in U.S. Plant Pat. No. 26,784. Plants of the new *Gerbera* differ from plants of 'Garglow Imp' in the following characteristics:

1. Plants of the new *Gerbera* have larger leaves than plants of 'Garglow Imp'.
2. Plants of the new *Gerbera* have smaller inflorescences than plants of 'Garglow Imp'.
3. Ray florets of plants of the new *Gerbera* are lighter orange in color than ray florets of plants of 'Garglow Imp'.

BRIEF DESCRIPTION OF THE PHOTOGRAPH

The accompanying photograph illustrates the overall appearance of the new *Gerbera* plant showing the colors as true as it is reasonably possible to obtain in colored reproductions of this type. Colors in the photograph may differ slightly from the color values cited in the detailed botanical description which accurately describe the colors of the new *Gerbera* plant. The photograph comprises a side perspective view of a typical flowering plant of 'Garsweetcaro' grown in a container.

DETAILED BOTANICAL DESCRIPTION

The aforementioned photograph and following observations and measurements describe plants grown during the autumn and winter in 19-cm containers in a glass-covered greenhouse in De Kwakel, The Netherlands and under cultural practices typical of commercial garden *Gerbera* production. During the production of the plants, day temperatures ranged from 12° C. to 15° C. and night temperatures averaged 15° C. Plants were six months old when the photograph was taken and 20 weeks old when the description was taken. In the following description, color references are made to The Royal Horticultural Society Colour Chart, 2015 Edition, except where general terms of ordinary dictionary significance are used.

Botanical classification: *Gerbera hybrida* 'Garsweetcaro'.

Parentage:

*Female, or seed, parent*.—Proprietary selection of *Gerbera hybrida* identified as code number 08T013, not patented.

*Male, or pollen, parent*.—Proprietary selection of *Gerbera hybrida* identified as code number 09T231, not patented.

Propagation:

*Type*.—By cuttings and meristem culture.

*Time to initiate roots, by cuttings, summer and winter*.—About 3.5 weeks at temperatures about 20° C.

*Time to initiate roots, by tissue culture, summer and winter*.—About 2.5 to 3 weeks at temperatures about 20° C.

*Time to produce a rooted young plant, by cuttings, summer and winter*.—About 3.5 weeks at temperatures about 20° C. to 26° C.

*Time to produce a rooted young plant, by tissue culture, summer and winter*.—About five to six weeks at temperatures about 20° C.

*Root description*.—Fibrous; white in color.

Plant description:

*Appearance*.—Herbaceous perennial that is typically grown as a container or garden plant; compact and uniformly mounding plant habit; upright, broadly spreading and roughly flattened globular in shape; numerous leaves arranged in basal rosettes; dense and bushy habit; inflorescences held above the foliar plane on erect and strong basal scapes; low vigor to moderately vigorous growth habit.

*Plant height, soil level to top of foliar plane*.—About 18.8 cm.

*Plant height, soil level to top of inflorescences*.—About 34.9 cm.

*Plant width*.—About 39.6 cm.

Leaf description:

*Arrangement*.—Alternate, simple.

*Length*.—About 17.4 cm.

*Width*.—About 8.9 cm.

*Shape*.—Elliptical to narrowly ovate; runcinate; slightly curved.

*Apex*.—Obtuse.

*Base*.—Acuminate.

*Margin*.—Coarsely and irregularly angulate; sinuses medium to deep and divergent; undulate.

*Texture and luster, upper surface*.—Glabrous, moderately rugose; slightly glossy.

*Texture and luster, lower surface*.—Moderately to densely pubescent, slightly rugose; matte.

*Venation pattern*.—Pinnate.

*Color*.—Developing leaves, upper surface: Close to between NN137A and 141A. Developing leaves, lower surface: Close to between 138A and 147B. Fully expanded leaves, upper surface: Close to NN137A; venation, close to 144C. Fully expanded leaves, lower surface: Close to 147B; venation, close to 144A.

*Petioles*.—Length: About 6.7 cm. Diameter: About 3.5 mm. Texture and luster, upper and lower surfaces: Densely pubescent; slightly glossy. Strength: Moderate to strong. Color, upper surface: Close to 152D; fading proximally to close to 179C. Color, lower surface: Close to 152D; fading proximally to close to 179D.

Inflorescence description:

*Appearance*.—Single composite inflorescence form with oblanceolate-shaped ray florets; solitary inflorescences borne on upright and strong scapes and held above the foliar plane; ray and disc florets arranged acropetally on a capitulum; inflorescences face upright.

*Fragrance*.—None detected.

*Flowering season*.—Plants begin flowering about three months after planting; under garden conditions in The Netherlands, plants flower from spring to late autumn; plants can be flowered year-round in the greenhouse.

*Inflorescence longevity*.—Depending on the temperature, inflorescences last about three weeks on the plant; inflorescences persistent.

*Quantity of inflorescences*.—Freely flowering habit with about 14 open and developing inflorescences per plant at one time.

*Inflorescence buds*.—Height: About 1.2 cm. Diameter: About 1.8 cm. Shape: Flattened globular. Texture and luster: Moderately pubescent; slightly glossy. Color: Close to 143B and 143C; immature ray florets, close to 150C.

*Inflorescence size*.—Diameter: About 7.6 cm. Depth (height): About 2.8 cm. Diameter of disc: About 3.7 cm. Receptacle height: About 3 mm. Receptacle diameter: About 4 mm. Receptacle color: Close to 145D.

*Ray florets*.—Quantity and arrangement: About 60 per inflorescence arranged in about three whorls. Orientation: Proximally, about 40° from vertical; distally, close to horizontal. Length: About 3.5 cm. Width: About 6 mm. Shape: Oblanceolate. Apex: Finely emarginate to finely praemorse. Base: Narrowly cuneate. Margin: Entire. Texture and luster, upper surface: Smooth, glabrous; velvety; longitudinally ridged; matte. Texture and luster, lower surface: Smooth, glabrous; moderately velvety; longitudinally ridged; matte. Color: When opening, upper surface: Close to N25A; towards the apex, fading to close to 13A. When opening, lower surface: Close to 4A. Fully opened, upper surface: Close to 25A; towards the apex, fading to close to 9A; color not changing with development. Fully opened, lower surface: Close to 7D; color does not change with development.

*Disc florets*.—Quantity and arrangement: About 300 massed at center of receptacle in about eleven whorls. Length: About 1.2 cm. Width: About 5 mm. Shape: Tubular with upper two narrow free lobes and one broader free lobe. Apex: Acute; upper 42.5%, free. Base: Lower 57.5%, fused. Margin, free lobes: Entire. Texture, upper surface: Smooth, glabrous; slightly velvety; matte. Texture, lower surface: Smooth, glabrous; very slightly velvety; slightly glossy. Color: When opening, inner and outer surface: Proximally, close to 5D; distally, close to 5B. Fully opened, inner and outer surface: Proximally, close to 5D; distally, close to 7C to 7D; color becoming closer to N30B with development.

*Pappus*.—Quantity of hairs per floret: About 60. Length: About 7 mm. Diameter: Less than 1 mm. Texture and luster: Soft; matte. Color: Close to 161B to 161C.

*Phyllaries*.—Quantity and arrangement: About 60 per inflorescence arranged in about three whorls. Length: About 1.5 cm. Width (at base): About 2 mm. Shape: Ligulate. Apex: Narrowly acute. Base: Cuneate. Margin: Entire. Texture and luster, upper surface: Smooth, glabrous; moderately glossy. Texture and luster, lower surface: Sparsely to moderately pubescent; slightly glossy. Color, upper surface: Close to 143B. Color, lower surface: Close to 143A to 143B.

*Scapes*.—Length: About 32 cm. Diameter: Proximally, about 5 mm; distally, about 3.5 mm. Strength: Moderately strong. Angle: About 8° from vertical. Texture and luster: Moderately to densely pubescent; moderately glossy. Color: Proximally, close to 144A; distally, close to 147B.

*Reproductive organs*.—Androecium (present on disc florets only): Quantity per floret: Five. Filament length: About 6 mm. Filament color: Close to 150C to 150D. Anther shape: Ligulate; basifixed. Anther size: About 4 mm by 0.3 mm. Anther color: Close to 13A. Pollen amount: Scarce. Pollen color: Close to 13B. Gynoecium (present only on ray and disc florets): Quantity per floret: One. Pistil length: About 8.5 mm. Stigma diameter: About 0.5 mm. Stigma shape: Cleft. Stigma color: Close to 4C. Style length: About 8 mm. Style color: Close to 4D. Ovary color: Close to 157D.

*Seeds and fruits*.—Seed and fruit production has not been observed on plants of the new *Gerbera* to date.

Disease & pest resistance: Resistance to pathogens and pests common to *Gerbera* plants has not been observed on plants of the new *Gerbera* grown under commercial production conditions to date.

Garden performance: Plants of the new *Gerbera* have been observed to have good garden performance and to tolerate high temperatures about 35° C. and to be cold hardy to USDA Hardiness Zone 7.

It is claimed:

1. A new and distinct *Gerbera* plant named 'Garsweetcaro' as illustrated and described.

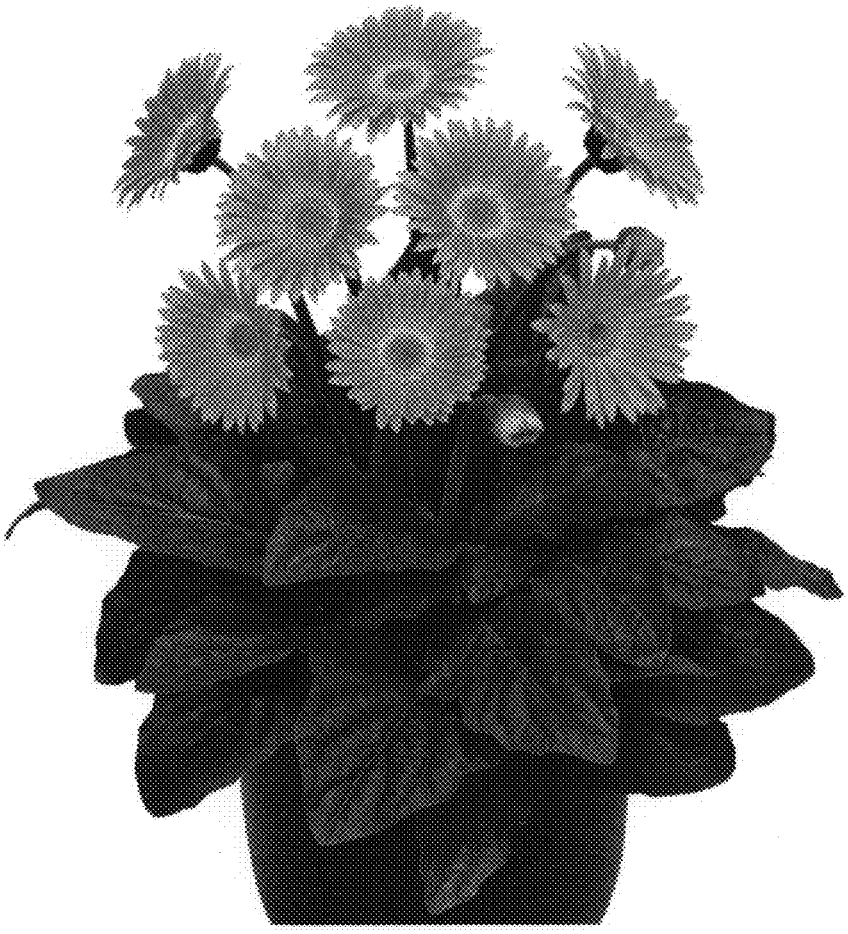

* * * * *